United States Patent
Wang et al.

(10) Patent No.: US 11,513,053 B2
(45) Date of Patent: Nov. 29, 2022

(54) METHOD FOR DETERMINING OPTIMAL PRESERVATION TEMPERATURE OF ANAEROBIC AMMONIUM OXIDATION BIOFILM IN WASTEWATER TREATMENT FOR TOTAL NITROGEN REMOVAL

(71) Applicant: Jiangnan University, Wuxi (CN)

(72) Inventors: Shuo Wang, Wuxi (CN); Yin Zhu, Wuxi (CN); Xuesong Yi, Wuxi (CN); Ji Li, Wuxi (CN); Yan Wang, Wuxi (CN); Junhua Zheng, Wuxi (CN)

(73) Assignee: Jiangnan University, Wuxi (CN)

(*) Notice: Subject to any disclaimer, the term of this patent is extended or adjusted under 35 U.S.C. 154(b) by 447 days.

(21) Appl. No.: 16/869,679

(22) Filed: May 8, 2020

(65) Prior Publication Data
US 2020/0264089 A1 Aug. 20, 2020

Related U.S. Application Data

(63) Continuation of application No. PCT/CN2019/102968, filed on Aug. 28, 2019.

(30) Foreign Application Priority Data

Sep. 18, 2018 (CN) .......................... 201811088026.0

(51) Int. Cl.
*G01N 15/14* (2006.01)
*B01D 71/56* (2006.01)
(Continued)

(52) U.S. Cl.
CPC ............ *G01N 15/14* (2013.01); *B01D 71/56* (2013.01); *C02F 3/102* (2013.01); *C02F 3/28* (2013.01);
(Continued)

(58) Field of Classification Search
None
See application file for complete search history.

(56) References Cited

U.S. PATENT DOCUMENTS

| | | | |
|---|---|---|---|
| 5,651,891 A * | 7/1997 | Molof | C02F 3/308 210/906 |
| 7,267,764 B2 * | 9/2007 | Isaka | C02F 3/302 210/194 |

(Continued)

FOREIGN PATENT DOCUMENTS

| | | |
|---|---|---|
| CN | 103293138 A | 9/2013 |
| CN | 103808703 A | 5/2014 |

(Continued)

OTHER PUBLICATIONS

Tian et al. "Nitrogen removal potential and biofilm characteristics in the anaerobic ammonium oxidation ('ANAMMOX') biofilter reactor", 2010 IEEE, 5 pages.*

(Continued)

*Primary Examiner* — Van H Nguyen
(74) *Attorney, Agent, or Firm* — IPro, PLLC; Na Xu

(57) ABSTRACT

The present disclosure discloses a method for determining optimal preservation temperature of the anaerobic ammonia oxidation biofilm in wastewater treatment, and belongs to the technical field of environmental engineering. The method of the present disclosure characterizes the ratio of living cells, early apoptotic cells, late apoptotic cells and dead cells in the anaerobic ammonia oxidation biofilm by flow cytometry, and the optimum storage temperature can be measured within a few hours. The method of the present disclosure performs correlation analysis on the characteristic indexes of the anaerobic ammonia oxidation biofilm activity recovery process to verify the reliability of the data. By using the method of the present disclosure, the step of (Continued)

recovering the biofilm activity can be omitted, the removal rates of ammonia nitrogen and total nitrogen were over 90% and 85%, respectively.

8 Claims, 2 Drawing Sheets

(51) Int. Cl.
*C02F 3/10* (2006.01)
*C02F 3/28* (2006.01)
*C02F 101/16* (2006.01)

(52) U.S. Cl.
CPC ...... *C02F 2101/16* (2013.01); *C02F 2209/02* (2013.01)

(56) References Cited

U.S. PATENT DOCUMENTS

| | | | | |
|---|---|---|---|---|
| 7,314,563 B2* | 1/2008 | Cho | ...... | C02F 3/1273 |
| | | | | 210/906 |
| 8,394,272 B2* | 3/2013 | Peng | ...... | C02F 3/301 |
| | | | | 210/615 |
| 8,864,993 B2* | 10/2014 | Zhao | ...... | C02F 3/341 |
| | | | | 210/906 |
| 2020/0048677 A1* | 2/2020 | Wang | ...... | C12Q 1/02 |

FOREIGN PATENT DOCUMENTS

| | | |
|---|---|---|
| CN | 104845997 A | 8/2015 |
| CN | 106635803 A | 5/2017 |
| JP | 2009058233 A | 3/2009 |

OTHER PUBLICATIONS

Ping et al. "Study on the Bioreactor for Removal of Nitrogen and Phosphorus in Wastewater", 2011 IEEE, 4 pages.*
CPT/CN2019/102968 ISR ISA210 dated Nov. 27, 2019.

* cited by examiner

US 11,513,053 B2

METHOD FOR DETERMINING OPTIMAL PRESERVATION TEMPERATURE OF ANAEROBIC AMMONIUM OXIDATION BIOFILM IN WASTEWATER TREATMENT FOR TOTAL NITROGEN REMOVAL

TECHNICAL FIELD

The present disclosure relates to a method for determining optimal preservation temperature of anaerobic ammonium oxidation biofilm in wastewater treatment for total nitrogen removal, and belongs to the technical field of environmental engineering.

BACKGROUND

The low content of organic pollutants in the inflow water of the wastewater treatment plant is always a technical difficulty for restricting the standard emission of total nitrogen, and simultaneously, along with the improvement of the emission standard of wastewater treatment, a large amount of soil is occupied by reconstruction and extension projects, a large amount of organic carbon source substances are added into a water body, so that the investment construction and operation cost are remarkably increased, and thus the energy saving and consumption reducing effects of the wastewater treatment plant are seriously influenced. Therefore, wastewater denitrification technologies based on land-saving objectives and low carbon source utilization are receiving increasing attention. The anaerobic ammonium oxidation technology refers to the process of anaerobic ammonia oxidizing bacteria oxidizing ammonia nitrogen using nitrite and finally generating nitrogen under anaerobic conditions. This process does not require additional carbon source, and anaerobic ammonia oxidizing bacteria can be better attached to the suspended filler. Therefore, anaerobic ammonia oxidation biofilm technology is of great significance for the operation of sewage treatment plants based on efficient nitrogen removal and energy saving.

However, in the actual operation of the project, the growth rate of anaerobic ammonia-oxidizing bacteria is low, and the generation time is long (about 15-20 days). If the anaerobic ammonia oxidizing bacteria can be attached to the suspension filler to form an anaerobic ammonium oxidation biofilm, and cultivated, matured and stored, the wastewater treatment plant with low carbon source in inflow water and short land resources can be effectively helped to start running in a short time, and ammonia nitrogen and total nitrogen can be discharged under the standard. The temperature is an important parameter influencing the activity of the anaerobic ammonium oxidation biofilm, and the temperature which is most suitable for storing the anaerobic ammonium oxidation biofilm is determined, so that the activity recovery process is simplified, the starting time of engineering application is shortened, and the energy saving and consumption reducing effects are realized. However, in the existing method, the optimum preservation temperature needs to be determined by re-inoculating the anaerobic ammonium oxidation biofilm into the bioreactor, and the time for determining the activity recovery effect of the anaerobic ammonium oxidation biofilm is about 8-35 d, and thus the long time consumption becomes important for restricting the engineering application of the method.

SUMMARY

In order to simplify the activity recovery process of the anaerobic ammonium oxidation biofilm, allow the ammonia nitrogen and total nitrogen indexes of the wastewater treatment plant to reach the standard for discharge in a short time and achieve the land saving, energy saving and consumption reducing effects at the same time, the present disclosure characterizes cell activity states in the anaerobic ammonium oxidation biofilms stored under different temperature conditions based on the flow cytometry, verifies the characterization result of the flow cytometry according to activity recovery effect of anaerobic ammonia oxidation biofilm and the cell activity states after recovering the activity of the biofilm, and finally establishes a method for determining the optimum preservation temperature of the anaerobic ammonia oxidation biofilm based on the flow cytometry, and provides technical support for high-standard pollutant discharge and energy saving and consumption reducing operation of the wastewater treatment plant.

A first object of the present disclosure is to provide a method for determining an optimum preservation temperature of an anaerobic ammonia oxidation biofilm, which comprises measuring the cell activity state of the anaerobic ammonia oxidation biofilm based on flow cytometry, comparing the measured results of the cell activity states of the anaerobic ammonia oxidation biofilm stored at different temperatures with those of the anaerobic ammonia oxidation biofilm before preservation, and taking the preservation temperature closest to the cell activity state of the anaerobic ammonia oxidation biofilm before preservation as the optimum preservation temperature.

In one embodiment of the present disclosure, the measurement of the cell activity state of the anaerobic ammonia oxidation biofilm comprises the measurement of the content of living cells, early apoptotic cells, late apoptotic cells and dead cells.

In one embodiment of the present disclosure, the step of determining the optimum temperature in the flow cytometry comprises:

(1) preparing an anaerobic ammonia oxidation biofilm test sample solution: taking the anaerobic ammonia oxidation biofilm sample in sludge dewatering filtrate treatment tank, diluting an anaerobic ammonia oxidation biofilm sample with a buffer, shaking evenly, filtering, centrifuging, leaving the supernatant, purging the cells with a pre-cooled phosphate buffer, repeating centrifugation and wash twice, then taking the supernatant as a sample, and mixing well with an appropriate amount of 10× Annexin V Binding Buffer;

(2) placing in a flow cytometer for measuring the cell activity state of each sample solution.

In one embodiment of the present disclosure, the buffer contains phosphate buffer and fetal bovine serum.

In one embodiment of the present disclosure, the phosphate buffer comprises 0.2 mol/L sodium dihydrogen phosphate and 0.2 mol/L disodium hydrogen phosphate.

In one embodiment of the present disclosure, the volume ratio of phosphate buffer and fetal bovine serum in the buffer is 8:1-10:1.

In one embodiment of the present disclosure, the pH of the buffer is 7.2-8.0, and the dilution ratio with the anaerobic ammonia oxidation biofilm is (8-10):1.

In one embodiment of the present disclosure, a nylon membrane having a pore size of 6-8 μm is used for filtration.

In one embodiment of the present disclosure, the centrifugation speed is 5000-10000 rpm.

In one embodiment of the present disclosure, the mixed volume ratio of the sample supernatant to the 10× Annexin V Binding Buffer is 1:2-4.

In one embodiment of the present disclosure, the measurement of the cell activity state of each sample solution by the flow cytometer is carried out by adding 0.5 μl PI staining agent to the control FITC Annexin V group, adding 0.5 μl FITC Annexin V to the control PI group, adding 0.5 μl FITC Annexin V and 0.5 μl PI to the test group, mixing well, incubating in the dark at room temperature, and then testing on a flow cytometer.

In one embodiment of the present disclosure, the incubation time is 10-20 min.

A second object of the present disclosure is to provide a method for rapidly initiating the anaerobic ammonia oxidation biofilm engineering, which comprises preliminarily culturing and maturing the anaerobic ammonia oxidation biofilm, placing in a preservation medium, storing at an optimum preservation temperature, and using for wastewater treatment after recovering the activity; the optimum temperature is determined by the above method for determining an optimum preservation temperature of an anaerobic ammonia oxidation biofilm.

In one embodiment of the present disclosure, the preservation medium has a $KHCO_3$ of 1500 mg/L, $K_2HPO_4$ of 15 mg/L, $MgSO_4$ of 180 mg/L, $CaCl_2$ of 20 mg/L, $NH_4^+$—N of 50 mg/L, and $NO_2^-$—N of 75 mg/L.

In an embodiment of the present disclosure, the activity recovery of the anaerobic ammonia oxidation biofilm comprises inoculating the anaerobic ammonia oxidation biofilm into a bioreactor. The bioreactor is pre-passed with $N_2$ to reduce the inhibition of oxygen to the anaerobic ammonia oxidation bacteria, and the Hydraulic Retention Time (HRT) is set to 4 h, and the filling ratio of the anaerobic ammonia oxidation biofilm suspension filler is 40%.

A third object of the present disclosure is to apply the above method for rapidly initiating the anaerobic ammonia oxidation biofilm engineering to wastewater treatment.

Advantageous Effects of the Present Disclosure

The present disclosure characterizes the proportion of living cells, early apoptotic cells, late apoptotic cells and dead cells of various biofilms through flow cytometry, determines the optimum preservation temperature within a few hours, performs correlation analysis on the characteristic indexes of the anaerobic ammonia oxidation biofilm activity recovery process, and establishes the method for determining the optimum preservation temperature of the anaerobic ammonia oxidation biofilm based on the flow cytometry. By using the method, the step of recovering the biofilm activity can be omitted, the wastewater treatment plant which intends to adopt the anaerobic ammonia oxidation biofilm process technology to discharge the ammonia nitrogen, total nitrogen under the standard is effectively helped to realize the land saving, energy saving and consumption reducing operation, and simultaneously, the starting time of engineering application of the anaerobic ammonia oxidation biofilm process can be effectively shortened, the long-term stable operation of the anaerobic ammonia oxidation biofilm process is maintained, and the method has high industrial feasibility.

DETAILED DESCRIPTION

Figure 1:
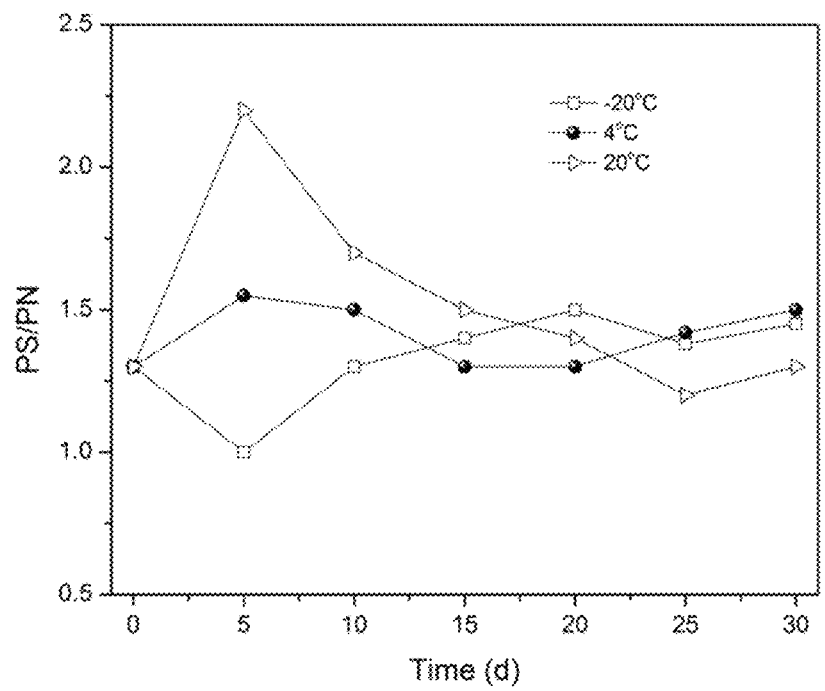
FIG. 1 shows changes in the extracellular polymer PN (protein)/PS (polysaccharide).

The wastewater of the wastewater treatment plant of the present disclosure includes domestic water in residential areas and a small part of industrial wastewater in the upstream, and the annual average of inflow water is COD of 236 mg/L, ammonia nitrogen of 30.1 mg/L, total nitrogen of 37.8 mg/L, and total phosphorus of 4.5 mg/L. The nitrate nitrogen content is less than 1.0 mg/L.

Example 1

Preservation Conditions of Anaerobic Ammonia Oxidation Biofilm:

The preservation temperature of the anaerobic ammonia oxidation biofilm was set to −20° C., 4° C. and 20° C. 150 of the anaerobic ammonia oxidation biofilm suspension filled in sludge dewatering filtrate treatment tank was taken out, divided into three equal portions and placed in 1000 mL serum bottles (the serum bottle is pre-filled with $N_2$ to expel $O_2$ from the air) containing 750 mL of preservation medium, respectively. The components of preservation medium were as follows: $KHCO_3$ of 1500 mg/L, $K_2HPO_4$ of 15 mg/L, $MgSO_4$ of 1800 mg/L, $CaCl_2$ of 20 mg/L, $NH_4^+$—$N(NH_4Cl)$ of 50 mg/L, and $NO_2^-$—$N(NaNO_2)$ of 75 mg/L. Serum bottles (3 parallel samples at each preservation temperature) were placed at −20° C., 4° C. and 20° C., and stored statically in the dark.

Cell State Characterization of Stored Anaerobic Ammonia Oxidation Biofilm:

Anaerobic ammonia oxidation biofilm stored at −20° C., 4° C. and 20° C. were stored for more than 120 days, and then used to determine the anaerobic ammonia oxidation biofilm cell status. Cell state test conditions by flow cytometry were as follows:

(1) Picked up 10 ml of anaerobic ammonia oxidation biofilm, diluted to 100 mL with a mixed buffer of pH 7.8 phosphate buffer and fetal bovine serum, and shaken for 2 min in a vortexer to break the biofilm into flocs and ensure a uniform distribution;

(2) The crushed sample was filtered through a nylon membrane having a pore size of 8 μm, and 1.5 mL was placed in a 1.5 mL sharp-bottomed centrifuge tube;

(3) The sample was centrifuged at 8000 rpm for 5 min;

(4) The supernatant of the sample after centrifugation was pipetted with leaving about 0.1 mL of sample, the cells were purged with pre-cooled mixed buffer of pH 7.8 phosphate buffer and fetal bovine serum (pH 7.8), and the centrifugation and wash were repeated twice;

(5) The supernatant of the sample after centrifugation was pipetted with leaving about 0.1 mL of sample, and mixed well with 0.3 mL of 10× Annexin V Binding Buffer;

(6) 0.5 μL of PI staining agent was added to the control FITC Annexin V group, 0.5 μL of FITC Annexin V was added to the control PI group, 0.5 μL of FITC Annexin V and 0.5 μL of PI were added to the test group, which were mixed well and incubated for 15 min at room temperature in the dark, and then tested on a flow cytometer.

The cell state results of anaerobic ammonia oxidation biofilm were shown in Table 1. The living cell proportion of the anaerobic ammonia oxidation biofilm suspension filled in sludge dewatering filtrate treatment tank was higher, indicating that the sludge dewatering filtrate of sewage treatment plant has good treatment effect on high ammonia nitrogen. The anaerobic ammonia oxidation biofilm stored at 20° C. had the lowest living cell content, indicating that it was not suitable to store anaerobic ammonia oxidation biofilm at 20° C. The anaerobic ammonia oxidation biofilm stored at 4° C. had the highest proportion of living cell, reaching 65%, and had a proportion of late apoptotic cells and dead cells of about 17.8%, indicating that the preservation condition at 4° C. was more suitable for storing anaerobic ammonia oxidation biofilm. When the preservation temperature was −20° C., the living cell proportion of anaerobic ammonia oxidation biofilm was 50.1%, which was only 22.9% lower than that of the anaerobic ammonia oxidation biofilm stored at 4° C., but the late apoptotic cells and dead cells proportion of about 39.5%, indicating that it was not suitable to store anaerobic ammonia oxidation biofilm at −20° C. Therefore, it was preliminarily determined that 4° C. was the optimum temperature for storing anaerobic ammonia oxidation biofilm.

TABLE 1

Cell activity states (%) of anaerobic ammonia oxidation biofilm stored for 120 days

| Anaerobic ammonia oxidation biofilm | Living cells | Early apoptotic cells | Late apoptotic cells | Dead cells |
|---|---|---|---|---|
| Sludge dewatering filtrate of sewage treatment plant | 82.5 ± 4.8 | 3.7 ± 1.6 | 5.9 ± 2.1 | 7.9 ± 1.6 |
| Stored at −20° C. | 50.1 ± 3.0 | 20.8 ± 1.6 | 18.7 ± 1.9 | 10.4 ± 1.9 |
| Stored at 4° C. | 65.0 ± 3.5 | 17.2 ± 1.9 | 15.5 ± 2.1 | 2.3 ± 0.2 |
| Stored at 20° C. | 35.8 ± 3.5 | 28.6 ± 3.1 | 27.9 ± 3.0 | 7.7 ± 0.8 |

Example 2: Verification of the Test Results of Anaerobic Ammonia Oxidation Biofilm A bioreactor was selected for activity recovery. Specific operating conditions include:

The anaerobic ammonia oxidation biofilm derived from different serum bottles was inoculated into a bioreactor (effective volume of 10.0 L) for the activity recovery of the anaerobic ammonia oxidation biofilm. the anaerobic ammonia oxidation biofilm stored at −20° C., 4° C. and 20° C. was placed in bioreactor 1 (R1), bioreactor 2 (R2) and bioreactor 3 (R3), respectively. The bioreactor was pre-passed with $N_2$ to reduce the inhibition of oxygen to the anaerobic ammonia oxidation bacteria, and the HRT was set to 4 h, and the filling ratio of the anaerobic ammonia oxidation biofilm suspension filler was 40%.

Example 3: Characteristics of Anaerobic Ammonia Oxidation Biofilm after Activity Recovery After 30 days of activity recovery, the characteristics of anaerobic ammonia oxidation biofilm in R1, R2 and R3 were shown in Table 2. As shown in Table 2, after recovering the anaerobic ammonia oxidation biofilm, the density and particle size of anaerobic ammonia oxidation biofilm at 4° C. and −20° C. were close to those of anaerobic ammonia oxidation biofilm before preservation, but the density (p) and thickness (L) of the anaerobic ammonia oxidation biofilm stored at 20° C. decreased slightly. The mixed liquor suspended solid (MLSS) of anaerobic ammonia oxidation biofilm stored at different preservation temperatures was reduced, but after activity recovery, the MLSS of the anaerobic ammonia oxidation biofilm at 4° C. and −20° C. was close to the MLSS of the anaerobic ammonia before storage, indicating that anaerobic ammonia oxidation biofilm readapted to the environment and the biomass was stably increased. Generally, the specific ANAMMOX activity (SAA) and Heme C content of anaerobic ammonia oxidation biofilm were 0.27 gN/gMLVSS·d (MLVSS: mixed liquid volatile suspended solids) and 2.3 μmol/gVSS (VSS: volatile suspended solid), respectively. The domesticated anaerobic ammonia oxidation biofilm in the wastewater treatment plant will respectively take 32 d and 24 d to reach the same SAA and Heme C content. After the activity of the stored anaerobic ammonia oxidation biofilm was recovered, the anaerobic ammonia oxidation biofilm in R1 will respectively take 9 d and 13 d to reach the same SAA and Heme C content, the anaerobic ammonia oxidation biofilm in R2 will respectively take 7 d and 11 d to reach the same SAA and Heme C content, and the anaerobic ammonia oxidation biofilm in R3 will respectively take 11 d and 17 d to reach the same SAA and Heme C content, indicating that the anaerobic ammonia oxidation biofilm after the activity recovery all had better nitrogen removal effects, wherein the anaerobic ammonia oxidation biofilm stored at the temperature of 4° C. has the shortest activity recovery time and the condition at 4° C. was more suitable for storing the anaerobic ammonia oxidation biofilm.

TABLE 2

Properties of anaerobic ammonia oxidation biofilm after preservation and activity recovery

| | ρ (g/cm³) | L (μm) | MLSS (g/cm²) | MLVSS (g/m²) | Time (d) required for SAA to be more than 0.27 gN/gMLVSS · d | Time (d) required for Heme C content to be more than 2.3 μmol/gVSS |
|---|---|---|---|---|---|---|
| Before sludge preservation | 0.039 | 301 | 15.9 | 7.5 | 32 | 24 |
| After anaerobic ammonia oxidation biofilm preservation | | | | | | |
| After preservation at −20° C. | 0.025 | 251 | 13.1 | 6.2 | — | — |
| After preservation at 4° C. | 0.031 | 279 | 14.7 | 6.4 | — | — |
| After preservation at 20° C. | 0.020 | 205 | 13.3 | 5.9 | — | — |

TABLE 2-continued

Properties of anaerobic ammonia oxidation biofilm after preservation and activity recovery

| | ρ (g/cm³) | L (μm) | MLSS (g/cm²) | MLVSS (g/m²) | Time (d) required for SAA to be more than 0.27 gN/gMLVSS · d | Time (d) required for Heme C content to be more than 2.3 μmol/gVSS |
|---|---|---|---|---|---|---|
| After activity recovery of the anaerobic ammonia oxidation biofilm | | | | | | |
| Anaerobic ammonia oxidation biofilm stored at −20° C. | 0.038 | 289 | 14.5 | 7.3 | 9 | 13 |
| Anaerobic ammonia oxidation biofilm stored at 4° C. | 0.040 | 297 | 15.4 | 7.2 | 7 | 11 |
| Anaerobic ammonia oxidation biofilm stored at 20° C. | 0.035 | 268 | 14.5 | 6.8 | 11 | 17 |

Example 4: Settling Performance and Stability of Anaerobic Ammonia Oxidation Biofilm after Activity Recovery Extracellular polymer was an important factor in the formation of anaerobic ammonia oxidation biofilm, and the ratio (PN/PS) of protein (PN) substance to polysaccharide (PS) substance in extracellular polymer was an important index for measuring the structural stability of the anaerobic ammonia oxidation biofilm. The changes in the extracellular polymer PN/PS during activity recovery process of the anaerobic ammonia oxidation biofilm were shown in FIG. 1. Under different preservation temperatures, PN/PS difference was large, and the PN/PS ratio of the anaerobic ammonia oxidation biofilm in R1 showed a trend of decreasing first and then increasing, indicating that the anaerobic ammonia oxidation biofilm stored at −20° C. had a gradually restored stability. The PN/PS ratio of the anaerobic ammonia oxidation biofilm in R3 was obviously increased, and then gradually decreased and finally tended to be stable, indicating that it was not suitable to store anaerobic ammonia oxidation biofilm at 20° C. The PN/PS ratio fluctuation of the anaerobic ammonia oxidation biofilm in R2 is relatively small, indicating that the anaerobic ammonia oxidation biofilm stored at 4° C. had a high stability after recovering the activity, and the temperature was suitable for being used as the preservation temperature of the anaerobic ammonia oxidation biofilm.

Figure 2:
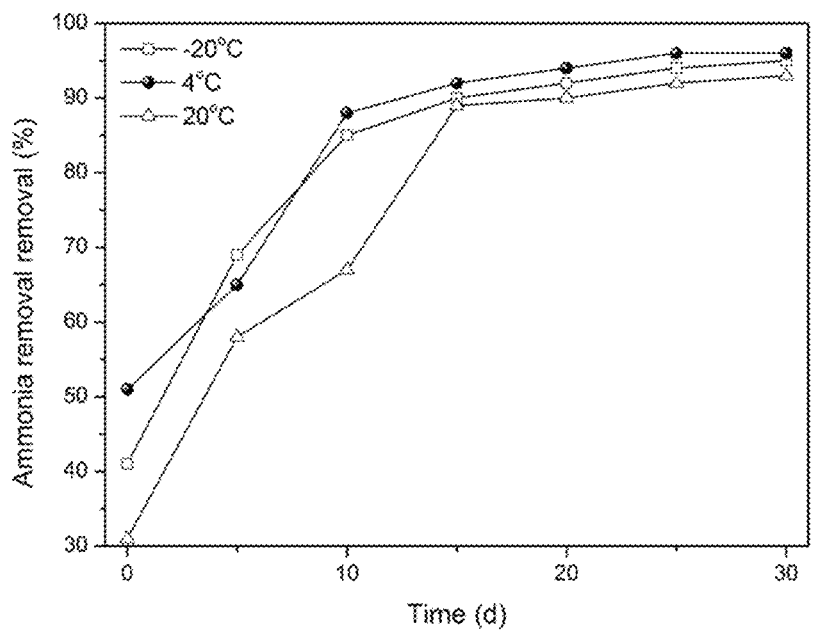
FIG. 2 shows the removal rate of ammonia nitrogen (AN).
Figure 3:
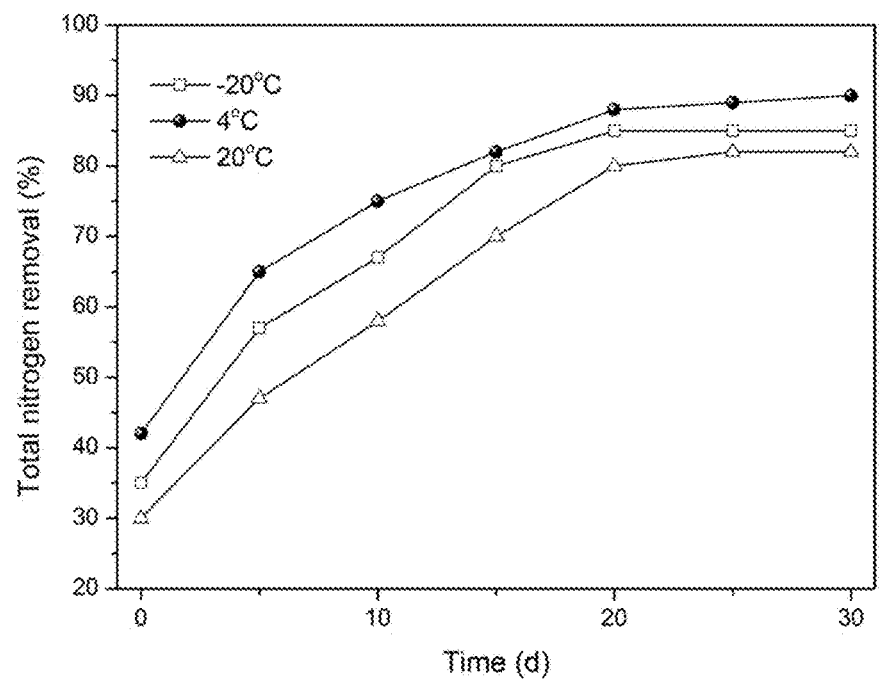
FIG. 3 shows the removal rate of total nitrogen (TN).

Example 5: Removal Efficiency of Pollutants by Anaerobic Ammonia Oxidation Biofilm after Activity Recovery After the activity recovery process, the removal rates of ammonia nitrogen (AN) and total nitrogen (TN) by anaerobic ammonia oxidation biofilm at different preservation temperatures were gradually increased (FIG. 2 and FIG. 3), and the removal rates of ammonia nitrogen and total nitrogen were over 90% and 85%, respectively. On the $12^{th}$ day after the activity recovery, the anaerobic ammonia oxidation biofilm in R2 had the best removal effect on AN and TN, and the AN and TN removal rates showed a steady increase trend. This result also corresponded to the fastest recovery of the higher SAA and Heme C content by the anaerobic ammonia oxidation biofilm in R2 in Table 2, indicating that the condition at 4° C. was more suitable for storing anaerobic ammonia oxidation biofilm and was highly feasible in practical applications.

Example 6: Correlation Between Anaerobic Ammonia Oxidation Biofilm Characteristics and Cell States after Activity Recovery After 30 d of anaerobic ammonia oxidation biofilm activity recovery, flow cytometry was used to analyze the anaerobic ammonia oxidation biofilm cell states (as shown in Table 3). The living cell content in anaerobic ammonia oxidation biofilm at different preservation temperatures was basically the same as the content of living cells in the anaerobic ammonia oxidation biofilm of the pilot system, indicating that all of the anaerobic ammonia oxidation biofilm after the activity recovery can play the role of nitrogen removal. Among them, the proportion of anaerobic ammonia oxidation biofilm living cells in R2 was the highest (85.1%±5.0%), and the proportion of late apoptotic cells 6.1%±1.8%) and the proportion of dead cells (3.7%±0.3%) were the lowest, indicating the anaerobic ammonia oxidation biofilm cells stored at 4° C. had the highest cell activity and 4° C. was more suitable as a condition for storing anaerobic ammonia oxidation biofilm.

TABLE 3

Cell activity states (%) of anaerobic ammonia oxidation biofilm cells after activity recovery (30 d)

| Anaerobic ammonia oxidation biofilm | Living cells | Early apoptotic cells | Late apoptotic cells | Dead cells |
|---|---|---|---|---|
| Sludge dewatering filtrate of sewage treatment plant | 87.5 ± 5.1 | 4.9 ± 1.1 | 5.1 ± 1.2 | 2.5 ± 0.5 |
| Stored at −20° C. | 83.0 ± 4.5 | 5.8 ± 1.7 | 6.1 ± 1.9 | 5.1 ± 1.0 |
| Stored at 4° C. | 85.1 ± 5.0 | 5.1 ± 1.6 | 6.1 ± 1.8 | 3.7 ± 0.3 |
| Stored at 20° C. | 80.3 ± 5.5 | 5.5 ± 1.5 | 8.9 ± 1.2 | 5.3 ± 1.0 |

According to Correl correlation analysis, it was found that the SAA and the Heme C content of Anaerobic ammonia oxidation biofilm had a very high correlation with the proportion of anaerobic ammonia oxidation biofilm living cells (as shown in Table 4), and the correlation coefficients were 0.9974 and 0.9930, respectively, indicating that the use of the proportion of anaerobic ammonia oxidation biofilm living cells as a method for evaluating the activity of anaerobic ammonia oxidation biofilm was extremely feasible. At the same time, in the stored anaerobic ammonia oxidation biofilm, the proportion of anaerobic ammonia oxidation biofilm living cells was the highest under the preservation condition of 20° C., which was consistent with results for the proportion of anaerobic ammonia oxidation biofilm living cells in R2 after activity recovery.

TABLE 4

Correlation between anaerobic ammonia oxidation biofilm characteristics and cell activity sates after activity recovery

|  | Anaerobic ammonia oxidation biofilm stored at −20° C. | Anaerobic ammonia oxidation biofilm stored at 4° C. | Anaerobic ammonia oxidation biofilm stored at 20° C. |
| --- | --- | --- | --- |
| SAA (gN/gMLVSS · d) | 0.30 | 0.33 | 0.27 |
| Heme C content (μmol/gVSS) | 2.5 | 2.6 | 2.3 |
| Living cell proportion (%) | 83.0 ± 4.5 | 85.1 ± 5.0 | 80.3 ± 5.5 |
| Correlation between SAA and living cells |  | 0.9974 |  |
| Correlation between Heme C content with living cells |  | 0.9930 |  |

Therefore, it was determined that 4° C. was the most suitable condition for storing anaerobic ammonia oxidation biofilm, and flow cytometry can be used as the basis for determining the optimum preservation temperature of anaerobic ammonia oxidation biofilm. Flow cytometry is easy to operate, the data are fast and easy to obtain, accurate and reliable, and the anaerobic ammonia oxidation biofilm activity recovery process can be omitted, which is of great significance for the preservation and activity recovery of anaerobic ammonia oxidation biofilm.

Example 7

Preservation Conditions of Anaerobic Ammonia Oxidation Biofilm:

The preservation temperature of the anaerobic ammonia oxidation biofilm was set to −20° C., 4° C. and 20° C. 150 of the anaerobic ammonia oxidation biofilm suspension filled in sludge dewatering filtrate treatment tank was taken out, divided into three equal portions and placed in 1000 mL serum bottles (the serum bottle is pre-filled with $N_2$ to expel $O_2$ from the air) containing 750 mL of preservation medium, respectively. The components of preservation medium were as follows: $KHCO_3$ of 1500 mg/L, $K_2HPO_4$ of 15 mg/L, $MgSO_4$ of 1800 mg/L, $CaCl_2$ of 20 mg/L, $NH_4^+$—$N(NH_4Cl)$ of 50 mg/L, and $NO_2^-$—$N(NaNO_2)$ of 75 mg/L. Serum bottles (3 parallel samples at each preservation temperature) were placed at −20° C., 4° C. and 20° C., and stored statically in the dark.

Cell State Characterization of Stored Anaerobic Ammonia Oxidation Biofilm:

Anaerobic ammonia oxidation biofilm stored at −20° C., 4° C. and 20° C. were stored for more than 120 days, and then used to determine the anaerobic ammonia oxidation biofilm cell status. Cell state test conditions by flow cytometry were as follows:

(1) Picked up 10 mL of anaerobic ammonia oxidation biofilm, diluted to 100 mL with phosphate buffer of pH 7.8, and shaken for 2 min in a vortexer to break the biofilm into flocs and ensure a uniform distribution;

(2) The crushed sample was filtered through a nylon membrane having a pore size of 8 μm, and 1.5 mL was placed in a 1.5 mL sharp-bottomed centrifuge tube;

(3) The sample was centrifuged at 8000 rpm for 5 min;

(4) The supernatant of the sample after centrifugation was pipetted with leaving about 0.1 mL of sample, the cells were purged with pre-cooled phosphate buffer (pH 7.8), and the centrifugation and wash were repeated twice;

(5) The supernatant of the sample after centrifugation was pipetted with leaving about 0.1 mL of sample, and mixed well with 0.3 mL of 10× Annexin V Binding Buffer;

(6) 0.5 μL of PI staining agent was added to the control FITC Annexin V group, 0.5 μL of FITC Annexin V was added to the control PI group, 0.5 μL of FITC Annexin V and 0.5 μL of PI were added to the test group, which were mixed well and incubated for 15 min at room temperature in the dark, and then tested on a flow cytometer.

The cell state results of anaerobic ammonia oxidation biofilm were shown in Table 5.

TABLE 5

Cell activity states (%) of anaerobic ammonia oxidation biofilm stored for 120 days (the buffer was pH 7.8 phosphate buffer)

| Anaerobic ammonia oxidation biofilm | Living cells | Early apoptotic cells | Late apoptotic cells | Dead cells |
| --- | --- | --- | --- | --- |
| Stored at −20° C. | 52.5 ± 8.0 | 19.7 ± 3.5 | 16.3 ± 3.9 | 11.5 ± 2.7 |
| Stored at 4° C. | 62.5 ± 8.5 | 16.2 ± 3.9 | 18.8 ± 3.5 | 2.5 ± 1.5 |
| Stored at 20° C. | 40.5 ± 5.5 | 25.7 ± 5.1 | 29.1 ± 3.6 | 4.7 ± 2.3 |

From the results of Table 5, it was found that the difference data in cell activity measured by using pH 7.8 phosphate buffer as the buffer under different temperatures, was significantly weaker than the activity data results measured by using the same pH phosphate buffer-fetal bovine serum mixed buffer as the buffer. The activity data measured by using pH 7.8 phosphate buffer as the buffer, has a large numerical deviation and a wide fluctuation range, which will significantly affect the results of flow cytometry. Combined with the weak variability of cell activity data at different storage temperatures, it was easy to cause large deviations in the end, and the test results and verification results did not match. Finally, flow cytometry cannot be used as a basis for effective storage temperature judgment.

At the same time, the pH of the buffer solution had a greater influence on the state of the cells during the test. It was the environment with weak alkaline pH 7.2-8.0 that had a good effect on the analysis of cell activity data, while the neutral acidity or excessive alkaline conditions had a small gap between the cell status data below, and the result cannot be accurately judged.

In addition, the anaerobic ammonia oxidation biofilm samples were respectively prepared with pore sizes of 6 μm and 10 μm, and it was found that the analysis results of the sample prepared with pore size of 6 μm were consistent with the verification experiment, and the data was reliable; the corresponding data with 10 μm did not have analytical capacity and cannot be used to determine the optimum preservation temperature.

What is claimed is:

1. A method, comprising determining an optimum preservation temperature of an anaerobic ammonia oxidation biofilm through the following steps:
measuring a cell activity state of the anaerobic ammonia oxidation biofilm based on flow cytometry;
comparing measured results of the cell activity states of the anaerobic ammonia oxidation biofilm preserved at different temperatures with those of the anaerobic ammonia oxidation biofilm before preservation; and
taking a preservation temperature closest to the cell activity state of the anaerobic ammonia oxidation biofilm before preservation as the optimum preservation temperature, wherein the measuring the cell activity state comprises measuring contents of living cells, early apoptotic cells, late apoptotic cells and dead cells;
wherein the measuring the cell activity state of the anaerobic ammonia oxidation biofilm based on the flow cytometry comprises:
(1) preparing a test sample solution of the anaerobic ammonia oxidation biofilm: diluting an anaerobic ammonia oxidation biofilm sample with a buffer, shaking evenly, filtering, centrifuging, leaving a supernatant, purging the cells with a pre-cooled phosphate buffer, repeating centrifugation and wash twice, then taking the supernatant as a sample, and mixing well with an appropriate amount of 10 x Annexin V Binding Buffer; wherein the buffer contains a phosphate buffer and fetal bovine serum, a pH value of the buffer is 7.2-8.0, and a dilution ratio with the anaerobic ammonia oxidation biofilm is (8-10):1; and
(2) placing in a flow cytometer for measuring a cell activity state of each sample solution;
wherein a nylon membrane having a pore size of 6-8 μm is used for filtration;
wherein the method further comprises initiating anaerobic ammonia oxidation biofilm engineering after determining an optimum preservation temperature of an anaerobic ammonia oxidation biofilm, and preliminarily culturing and maturing the anaerobic ammonia oxidation biofilm; placing in a preservation medium and preserving at the optimum preservation temperature; recovering activity; and using for an engineering application.

2. The method according to claim 1, wherein the measuring the cell activity state of the anaerobic ammonia oxidation biofilm based on the flow cytometry comprises:
(1) preparing a test sample solution of the anaerobic ammonia oxidation biofilm: diluting an anaerobic ammonia oxidation biofilm sample with a buffer, shaking evenly, filtering, centrifuging, leaving a supernatant, purging the cells with a pre-cooled phosphate buffer, repeating centrifugation and wash twice, then taking the supernatant as a sample, and mixing well with an appropriate amount of 10 x Annexin V Binding Buffer; and
(2) placing in a flow cytometer for measuring a cell activity state of each sample solution.

3. The method according to claim 2, wherein the buffer contains a phosphate buffer and fetal bovine serum.

4. The method according to claim 3, wherein a volume ratio of the phosphate buffer and fetal bovine serum in the buffer is 8:1-10:1.

5. The method according to claim 2, wherein the phosphate buffer comprises 0.2 mol/L of sodium dihydrogen phosphate and 0.2 mol/L of disodium hydrogen phosphate.

6. The method according to claim 2, wherein a pH value of the buffer is 7.2-8.0, and a dilution ratio with the anaerobic ammonia oxidation biofilm is (8-10):1.

7. The method according to claim 2, wherein a nylon membrane having a pore size of 6-8 μm is used for filtration.

8. The method according to claim 1, wherein the preservation medium has 1500 mg/L of $KHCO_3$, 15 mg/L of $K_2HPO_4$, 180 mg/L of $MgSO_4$, 20 mg/L of $CaCl_2$, 50 mg/L of $NH_4^+$—N, and 75 mg/L of $NO_2^-$—N.

* * * * *